United States Patent
Mortara et al.

(10) Patent No.: US 10,504,620 B2
(45) Date of Patent: *Dec. 10, 2019

(54) MEDICAL REPORTING SYSTEM AND METHOD

(71) Applicant: Welch Allyn, Inc., Skaneateles Falls, NY (US)

(72) Inventors: Justin Mortara, Milwaukee, WI (US); Scott Dorsey, Milwaukee, WI (US)

(73) Assignee: Welch Allyn, Inc., Skaneateles Falls, NY (US)

(*) Notice: Subject to any disclaimer, the term of this patent is extended or adjusted under 35 U.S.C. 154(b) by 112 days.

This patent is subject to a terminal disclaimer.

(21) Appl. No.: 15/932,210

(22) Filed: Feb. 16, 2018

(65) Prior Publication Data

US 2018/0190372 A1 Jul. 5, 2018

Related U.S. Application Data

(63) Continuation of application No. 14/020,615, filed on Sep. 6, 2013, now Pat. No. 9,898,586.

(51) Int. Cl.
*G06F 19/24* (2011.01)
*G16H 15/00* (2018.01)
(Continued)

(52) U.S. Cl.
CPC .......... *G16H 15/00* (2018.01); *G06F 17/243* (2013.01); *G06F 17/00* (2013.01); *G06F 17/24* (2013.01);
(Continued)

(58) Field of Classification Search
CPC ........ G16H 15/00; G16H 10/40; G16H 70/00; G16H 10/65; G16H 10/60; G06F 17/243;
(Continued)

(56) References Cited

U.S. PATENT DOCUMENTS 5,896,321 A 4/1999 Miller et al.
7,461,006 B2 12/2008 Gogolak
(Continued)

OTHER PUBLICATIONS

Aldosari et al., Constrained Association Rules for Medical Data, Journal of Applied Sciences, 2012, 9 pages.
(Continued)

*Primary Examiner* — Jason S Tiedeman
(74) *Attorney, Agent, or Firm* — Lee & Hayes, P.C.

(57) ABSTRACT

Systems and methods for use in providing input relating to medical data are provided. A method includes receiving a partial textual input relating to medical data. The method further includes determining one or more suggested input strings associated with the partial textual input. Determining the suggested input string(s) includes: (1) for each of a plurality of reference input strings contained within one or more of a plurality of reference files within a database, identifying a frequency with which the reference input string appears in the plurality of reference files, and (2) determining the suggested input string(s) further includes determining the suggested input string(s) from among the plurality of reference input strings based on the frequencies with which the reference input strings appear in the plurality of reference files. The method further includes providing the suggested input string(s) to the user as suggestions for completing the partial textual input.

20 Claims, 6 Drawing Sheets

(51) Int. Cl.
*G06F 17/24* (2006.01)
*G06F 19/00* (2018.01)
*G06Q 50/24* (2012.01)
*G06Q 50/22* (2018.01)
*G06F 17/00* (2019.01)
*G16H 10/65* (2018.01)
*G16H 10/60* (2018.01)
*G16H 70/00* (2018.01)
*G16H 10/40* (2018.01)

(52) U.S. Cl.
CPC ........... *G06F 19/324* (2013.01); *G06Q 50/22* (2013.01); *G06Q 50/24* (2013.01); *G16H 10/40* (2018.01); *G16H 10/60* (2018.01); *G16H 10/65* (2018.01); *G16H 70/00* (2018.01)

(58) Field of Classification Search
CPC ........ G06F 17/00; G06F 17/24; G06F 19/324; G06Q 50/22; G06Q 50/24
USPC .................. 705/2, 3; 715/221, 224–226, 780
See application file for complete search history.

(56) References Cited

U.S. PATENT DOCUMENTS

| | | | |
|---|---|---|---|
| 7,953,692 B2 | 5/2011 | Bower et al. | |
| 8,073,869 B2 | 12/2011 | Li et al. | |
| 8,195,594 B1 | 6/2012 | Bryce | |
| 8,275,759 B2 | 9/2012 | Imig et al. | |
| 8,380,723 B2 | 2/2013 | Radlinski | |
| 8,799,763 B1 | 8/2014 | Singh et al. | |
| 2004/0059237 A1 | 3/2004 | Narayan et al. | |
| 2005/0027566 A1* | 2/2005 | Haskell | G06F 17/2735 705/2 |
| 2005/0131686 A1 | 6/2005 | Yamamoto et al. | |
| 2005/0182336 A1 | 8/2005 | Sippens Groenewegen | |
| 2005/0192792 A1 | 9/2005 | Carus et al. | |
| 2006/0136263 A1 | 6/2006 | Fry et al. | |
| 2006/0167872 A1 | 7/2006 | Parikh | |
| 2007/0185544 A1 | 8/2007 | Dawant et al. | |
| 2008/0076472 A1 | 3/2008 | Hyatt | |
| 2008/0155398 A1 | 6/2008 | Bodin et al. | |
| 2008/0243542 A1 | 10/2008 | Hammond et al. | |
| 2008/0310723 A1 | 12/2008 | Manu et al. | |
| 2009/0019395 A1 | 1/2009 | Radom et al. | |
| 2010/0081953 A1 | 4/2010 | Syeda-Mahmood et al. | |
| 2010/0114887 A1 | 5/2010 | Conway et al. | |
| 2010/0130236 A1 | 5/2010 | Sivadas et al. | |
| 2010/0257166 A1 | 10/2010 | Ma | |
| 2010/0312549 A1 | 12/2010 | Akuwudike | |
| 2011/0082377 A1 | 4/2011 | Mahajan et al. | |
| 2011/0125743 A1 | 5/2011 | Immonen et al. | |
| 2011/0161311 A1 | 6/2011 | Mishne et al. | |
| 2011/0191270 A1 | 8/2011 | Peng et al. | |
| 2011/0213257 A1 | 9/2011 | Mahmood et al. | |
| 2011/0219299 A1 | 9/2011 | Scalosub | |
| 2012/0173261 A1 | 7/2012 | Schneider | |
| 2013/0085405 A1 | 4/2013 | Bera et al. | |
| 2013/0110553 A1 | 5/2013 | Navani et al. | |
| 2013/0190637 A1 | 7/2013 | Zhang et al. | |
| 2014/0163954 A1 | 6/2014 | Joshi et al. | |

OTHER PUBLICATIONS

Childs et al., Description of a Rule-Based System for the i2b2 Challenge in Natural Language Processing for Clinical Data, Journal of the American Medical Informatics Association, Jul./Aug. 2009, 5 pages.
Denny et al., Identifying QT Prolongation from ECG Impressions Using a General-Purpose Natural Language Processor, Int J Med Inform., Apr. 2009, 18 pages.
Ordonez et al., Discovering Interesting Association Rules in Medical Data, Proceedings of ACM SIGMOD Workshop on Research Issues on Data Mining and Knowledge Discovery, 2000, 8 pages.
Smartype News, Smartype Maximizes Transcription Productivity, www.smartype.com, Jan. 17, 2012, 2 pages.
Wennerberg et al., Interactive Clinical Query Derivation and Evaluation, Association for the Advancement of Artificial Intelligence, 2009, 5 pages.
Yang, Expert Network: Effective and Efficient Learning from the Human Decisions in Text Categorization and Retrieval, Research and Development in Information Retrieval, 1994, 10 pages.

\* cited by examiner

| Interpretation | Serial Comparison | History |

SINUS BRADYCARDIA
RIGHT BUNDLE BRANCH BLOCK
LEFT VENTRICULAR HYPERTROPHY AND ST-T CHANGE
INTERPRETATION BASED ON A DEFAULT AGE OF 40 YEARS

ABNORMAL ECG ▼  UNCONFIRMED REPORT

| Interpretation | Serial Comparison | History |

A

710 {
ATRIAL FIBRILLATION
ATRIAL FIBRILLATION WITH RAPID VENTRICULAR RESPONSE
ATRIAL FIBRILLATION WITH ABERRANT CONDUCTION OR VENTRICULA...
ARM LEADS REVERSED
ATRIAL FIBRILLATION WITH RAPID VENTRICULAR RESPONSE WITH ABE...
ATRIAL FIBRILLATION WITH SLOW VENTRICULAR RESPONSE
ABNORMAL QRS-T ANGLE

| Interpretation | Serial Comparison | History | s

805 {
SINUS RHYTHM
SINUS BRADYCARDIA
SINUS TRACHYCARDIA
ST DEVIATION AND MODERATE T-WAVE ABNORMALITY, CONSIDER LAT...
SINUS RHYTHM WITH FIRST DEGREE AV BLOCK
SINUS RHYTHM WITH SINUS ARRHYTHMIA
ST DEVIATION AND MODERATE T-WAVE ABNORMALITY, CONSIDER INFE...

| Interpretation | Serial Comparison | History |

R

905 {
RIGHT BUNDLE BRANCH BLOCK
RIGHT ATRIAL ENLARGEMENT
RIGHT AXIS DEVIATION
RIGHT VENTRICULAR HYPERTROPHY
RIGHT VENTRICULAR HYPERTROPHY AND ST-T CHARGE
RIGHT BUNDLE BRANCH BLOCK AND POSSIBLE RIGHT VENTRICULAR H...
SINUS RHYTHM

MEDICAL REPORTING SYSTEM AND METHOD

CROSS-REFERENCE TO RELATED APPLICATION

This application is a continuation of U.S. application Ser. No. 14/020,615, filed Sep. 6, 2013, entitled "MEDICAL REPORTING SYSTEM AND METHOD," which is incorporated by reference herein in its entirety.

BACKGROUND

The present disclosure relates generally to the field of medical data entry. More particularly, the present disclosure relates to systems and methods that allow a user to more easily enter textual data in a medical environment.

Medical data reporting and/or analysis systems may present a user with one or more data entry fields in which a user can enter textual data relating to medical data. For example, an electrocardiogram (ECG) reporting system may present a physician with a visual representation of the ECG signal and provide an interface through which the physician can enter notes about the physician's observations, analysis, conclusions, etc. relating to the ECG image. There is a need for a method of assisting in this data entry process that allows the physician or other user to enter data more easily and efficiently.

SUMMARY

One embodiment of the disclosure relates to a method that includes receiving, at a computing device and from a user, a partial textual input relating to medical data (e.g., a medical image, such as an electrocardiogram (ECG) image). The partial textual input includes a string of one or more characters. The method further includes determining, using the computing device, one or more most clinically common input strings associated with the partial textual input. Determining the one or more most clinically common input strings includes, for each of a plurality of reference input strings contained within one or more of a plurality of reference files within a database, identifying a frequency with which the reference input string appears in the plurality of reference files. The plurality of reference files include textual data relating to medical data. Determining the one or more most clinically common input strings further includes determining the one or more most clinically common input strings from among the plurality of reference input strings based on the frequencies with which the reference input strings appear in the plurality of reference files. The method further includes providing the one or more most clinically common input strings to the user as suggestions for completing the partial textual input.

Another embodiment relates to a system including an electronic processor operably coupled to at least one memory and configured to receive, from a user, a partial textual input relating to medical data. The partial textual input includes a string of one or more characters. The electronic processor is further configured to determine one or more suggested input strings associated with the partial textual input by: (1) for each of a plurality of reference input strings contained within one or more of a plurality of reference files within a database, identifying a frequency with which the reference input string appears in the plurality of reference files, and (2) determining the one or more suggested input strings from among the plurality of reference input strings based on the frequencies with which the reference input strings appear in the plurality of reference files. The plurality of reference files include textual data relating to medical data. The electronic processor is further configured to provide the one or more suggested input strings to the user as suggestions for completing the partial textual input.

Another embodiment relates to one or more computer-readable storage media having instructions stored thereon that are executable by one or more processors to receive, from a user, a partial textual input relating to a medical image. The partial textual input includes a string of one or more characters. The instructions further cause the one or more processors to determine one or more suggested input strings associated with the partial textual input by: (1) for each of a plurality of reference input strings contained within one or more of a plurality of reference files within a database, identifying a frequency with which the reference input string appears in the plurality of reference files, and (2) determining the one or more suggested input strings from among the plurality of reference input strings based on the frequencies with which the reference input strings appear in the plurality of reference files. The plurality of reference files include textual data relating to medical images. The instructions further cause the one or more processors to provide the one or more suggested input strings to the user as suggestions for completing the partial textual input.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Referring generally to the figures, systems and methods that may be used to help a user (e.g., a physician) easily and efficiently enter textual input relating to medical data are shown and described according to various exemplary embodiments. Medical data analysis and/or reporting systems may allow a user, such as a physician, to enter and/or edit textual information relating to medical data, such as a medical image. In some embodiments, the system may display medical data to the user and allow the user to enter text relating to the displayed medical data. In some embodiments, the system may analyze the medical data (e.g., image) and/or a signal associated with the medical data and pre-populate one or more input fields with suggested textual analysis relating to the medical data. The user may revise the pre-populated text and/or add his or her own text to a textual input field to provide analysis, observations, annotations, etc. relating to the medical data.

Adding this textual input requires time and effort from the user. In some embodiments, the system may be configured to provide recommendations to the user upon the entry of a partial text string that may be used to complete the text string. In some such embodiments, the system may be configured to provide one or more suggested text strings in an alphabetical order, or by identifying reference text strings that are the closest text matches to the partial text string entered by the user. While these suggestions are based on the partial text input, they may not relate to the annotation that the user intended to enter.

The systems and methods presented herein are configured to provide suggestions based on data stored within a reference database. The reference database contains files that include text relating to medical data (e.g., sample medical image reporting files). Suggestions may be generated based in part on a frequency with which certain textual input strings appear in the reference files in the database. For example, a list of suggested input text strings may be provided for which the partial text input from the user matches a portion of the input string and the suggested input text strings appear with a relatively high frequency within the reference files in the database. Generating suggestions based on frequency of appearance within reference files (e.g., suggesting the most clinically common input strings, based on frequency of appearance within the reference files) may increase the likelihood that the suggestions presented to the users are the text strings that the user desires to use to complete the partial text input. Presenting the most clinically common input strings near the top of a list of suggested text strings may allow for more efficient data entry as opposed to providing suggestions based solely upon alphabetical order and/or text matching. In some embodiments, the suggestions provided may be based in part on a location into which the partial text is entered (e.g., which line of a text-entry field, which field in a multiple-field data entry form, etc.). In some embodiments, the suggestions may be customized to a particular individual or institution using the system (e.g., by using one or more reference files associated with the user, such as previous entries of the user). In some embodiments, the reference files used to generate the suggestions may be limited based on one or more characteristics of the medical data (e.g., medical image) or underlying signal (e.g., such that only reference files associated with medical images exhibiting the same characteristics are used to generate the suggestions).

Figure 1:
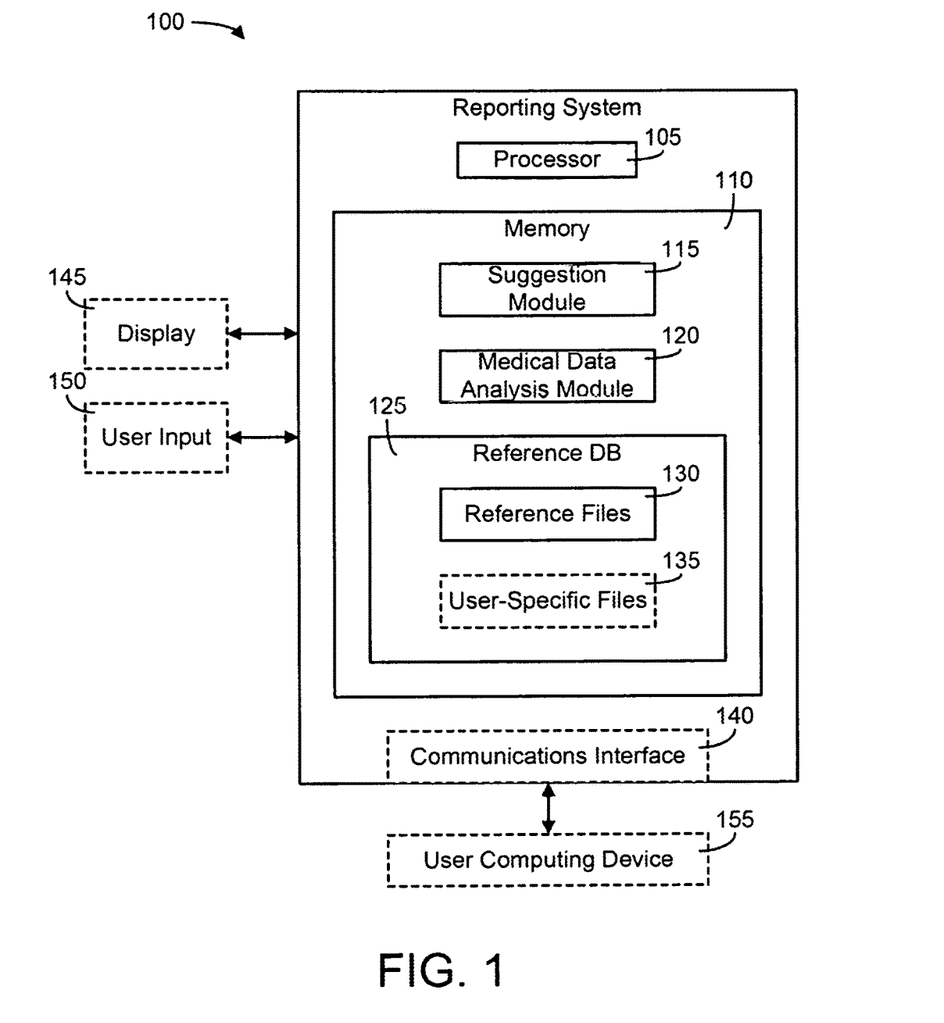
FIG. 1 is a block diagram of a reporting system configured to provide textual input suggestions relating to medical data according to an exemplary embodiment.

Referring now to FIG. 1, a block diagram of a reporting system 100 for entering textual data relating to medical data (e.g., medical images) is shown according to an exemplary embodiment. Reporting system 100 may provide a user with an interface through which the user can enter text and/or other types of annotations relating to medical data, such as one or more medical images (e.g., electrocardiogram (ECG) image, electroencephalogram (EEG) image, magnetic resonance image (MRI), positron emission tomography (PET) image, computed tomography (CT) image, ultrasound image, echocardiogram image, x-ray image, etc.). In some embodiments, system 100 may present the user with one or more medical images on a display device and receive observations, analysis, and/or other annotations from the user relating to the medical images. System 100 may store the textual input relating to the medical data within one or more data files. While the embodiments discussed herein are described with reference to text relating to medical image data, the present disclosure may also be applied to other types of medical data (e.g., non-image medical data) and/or non-medical data, as described in further detail below.

System 100 includes at least one processor 105, which may be any type of general purpose or special purpose processor (e.g., FPGA, CPLD, ASIC, etc.). System 100 also includes at least one memory 110, which may be any type of computer or machine-readable storage medium (e.g., ROM, RAM, hard disk, flash memory, etc.). In some embodiments, system 100 may be implemented as a client-side reporting system, for example, such that system 100 is implemented within a user device (e.g., a personal computer), data is displayed to the user on a display 145, and user input is received via a user input device 150 (e.g., mouse, keyboard, touchpad, voice inputs, etc.). In some embodiments, system 100 may be implemented as a server-side reporting system configured to receive partial text input entered by a user at a user computing device 155. In some such embodiments, system 100 may receive the partial text input from user computing device 155 over a network connection (e.g., LAN, WAN, etc.) at a communications interface 140 (e.g., Ethernet, WiFi, etc.), may generate suggestions based on the partial text input, and may transmit the suggestions back to user computing device 155.

Memory 110 may include one or more modules including instructions that may be executed by processor 105 to perform various processing functions for system 100. For example, memory 110 may include a suggestion module 115 configured to generate suggestions for text strings to complete partial text input. Suggestion module 115 may generate suggestions for completing the partial text input based in part on data in reference files 130 stored in a reference database 125. In some embodiments, reference database 125 may have a large number of reference files 130 (e.g., one million or more files).

In some embodiments, memory 110 may include a medical data analysis module 120 configured to analyze medical data (e.g., a medical image). For example, medical data analysis module 120 may analyze a medical image or underlying signal (e.g., using an automated image analysis method configured to identify one or more characteristics associated with the image) and generate one or more pre-populated text entries to be associated with the image. In some embodiments, a user may modify the pre-populated text entries, remove the text entries, and/or add new text entries. In some embodiments, medical data analysis module 120 may be configured to identify characteristics associated with an image based on the analysis, such as whether the image is associated with a particular condition or characteristic (e.g., a particular type of arrhythmia). In some embodiments, medical data analysis module 120 may be configured to analyze medical data other than image data, such as data relating to a treatment and/or medication history of a patient, and generate initial textual input based on the analysis and/or identify characteristics associated with the data.

Figure 2:
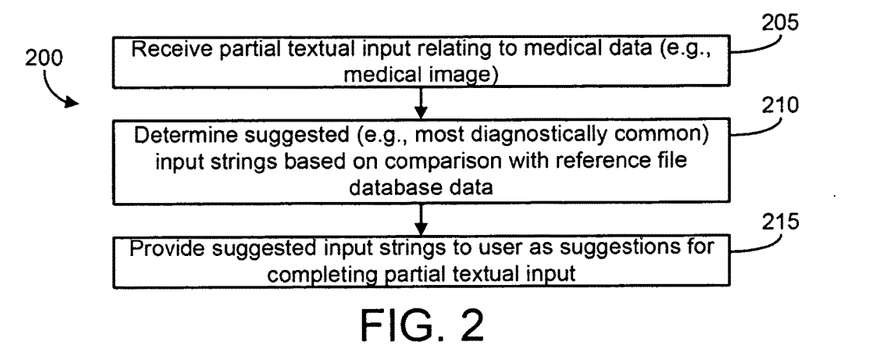
FIG. 2 is a flow diagram of a process for providing suggested input strings for completing a partial textual input according to an exemplary embodiment.

FIG. 2 illustrates a flow diagram of a process 200 for providing suggested input strings for completing a partial textual input according to an exemplary embodiment. Referring now to both FIGS. 1 and 2, system 100 may receive a partial textual input from a user relating to medical data (e.g., an ECG signal displayed to the user) (205). The partial textual input may include a string of one or more characters the user has entered within a text entry field. In some embodiments, medical data analysis module 120 may be configured to analyze the medical data or underlying signal(s) upon which the data is based and pre-populate one or more text entry fields with text based on the analysis. In such embodiments, the partial textual input from the user may include a modification to the pre-populated text entered by medical data analysis module 120 and/or a new text entry from the user in another portion of the text entry field(s).

System 100 may be configured to receive the partial textual input and determine one or more suggested input strings for completing the textual input based on data stored in reference database 125 (210). In some embodiments, system 100 may be configured to select suggested input strings that are the most clinically common input strings based on text entries provided within reference files 130 stored in database 125. Reference files 130 may each be files containing medical data (e.g., data relating to a medical image). For example, in some embodiments, reference files 130 may contain previously entered textual data relating to previously generated medical images or may contain sample or test data. In the event data relating to actual patients is included within reference files 130, the privacy of the data may be protected using one or more methods, such as encrypting the data, making the data anonymous (e.g., by allowing only aggregated data to be accessed by suggestion module 115, such that no individual's identity or characteristics can be discerned from the data), only including data in reference files 130 when a patient opts in to inclusion of his or her data, etc. The term "files," as used herein, includes separate data files, separate entries (e.g., containing a string of one or more characters) within a database or data file, and/or any other data container capable of representing and/or storing medical data. The suggested input strings may be provided to a user as suggestions for completing the partial textual input (215). The user may select one or more of the suggestions, and system 100 may replace the partial textual input with the selected suggestion(s) in the text entry field.

Figure 3:
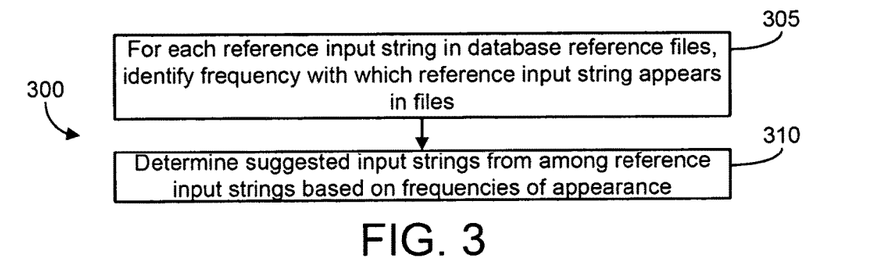
FIG. 3 is a flow diagram of a process for determining suggested input strings based on comparison of partial textual input with reference input from files in a database according to an exemplary embodiment.

FIG. 3 is a flow diagram of one process 300 that may be used to determine suggested input strings to complete the partial input based on a frequency of appearance of input strings within reference files 130 according to an exemplary embodiment. System 100 may be configured to identify a frequency with which certain reference input strings appear within reference files 130 (305). System 100 may be configured to identify reference strings based on an analysis (e.g., automated analysis) of the text contained in one or more text fields in reference files 130. For example, in some embodiments, system 100 may be configured to execute a text matching process to identify text strings appearing multiple times within reference files 130. In some embodiments, system 100 may only include a text string within the reference strings from which suggestions are to be determined when the text string meets certain criteria. For example, system 100 may be configured to exclude text strings from the frequency analysis and/or from consideration when determining suggestions when the text strings contain less than a predetermined number of words (e.g., three words). In another example, system 100 may exclude text strings when the strings contain only common words (e.g., the, in, at, on, etc.) and/or do not contain any terms of art (e.g., medical terms). For example, in some medical image-related embodiments, system 100 may exclude phrases from consideration as suggestions when they do not include terms relating to medical images (e.g., ECG rhythm-related statements). In some medication reporting embodiments, system 100 may exclude phrases from consideration as suggestions when they do not include terms relating to medications. Other criteria may be applied by system 100 in various embodiments. Such criteria may help ensure that the suggestions provided to the user are clinically relevant suggestions and not merely common phrases that happen to appear frequently within reference files 130.

For each of the reference input text strings to be analyzed, system 100 may determine a frequency with which the reference text appears in reference files 130. System 100 may be configured to measure and/or represent frequency of appearance in one or more of a variety of different manners. For example, system 100 may measure a number of occurrences of the reference text within the files, a number of files within which the reference text appears, a percentage of files within which the reference text appears, a number or percentage of text fields within the files in which the reference text appears, and/or any other quantitative measure representative of how frequent or common the reference text is within reference files 130. In some embodiments, this analysis may be performed in real-time by system 100 upon receipt of a partial textual input for which suggestions are to be provided. In some embodiments, this analysis may be performed prior to receipt of partial textual input, and the reference text strings and their respective frequency measures may be stored in a memory (e.g., in database 125) for retrieval and use upon receipt of partial textual input. In some embodiments, the analysis may be updated from time to time (e.g., periodically, upon addition/deletion of one or more reference files from database 125, etc.).

System 100 may be configured to determine one or more suggested input strings from among the reference input text strings based, at least in part, on the frequency measures associated with the reference text strings (310). In some embodiments, system 100 may determine suggestions based solely upon the frequency measures. For example, system 100 may identify any reference text strings containing the partial textual input (e.g., either at the beginning of the reference text string or anywhere within the reference text string) and select two or more of the reference text strings having the highest frequency values as the suggested input strings. System 100 may determine a number of suggestions to provide to the user using on one or more of a variety of methods, such as by selecting a predetermined number of reference text strings having the highest frequency values, selecting all reference text strings having frequency values above a particular threshold value, etc. In some embodiments, the suggestions may be presented to the user in a list. In some embodiments, the order of the suggestions in the list may be a descending order of frequency values.

In some embodiments, system 100 may determine suggested input strings based in part on the frequency measures and based in part on one or more other factors. For example, system 100 may configured to compare the partial textual input to the reference strings using a text matching process that analyzes the relevance of the reference strings to the partial textual input. The text matching process may determine strings that are most textually relevant based on whether the reference string includes a full match of the partial input, a match of one or more words of the partial input, a match of one or more synonyms of words in the partial input, etc. In some embodiments, the text matching process may operate in a manner similar to text matching processes used to determine relevant resources (e.g., web pages) to display to a user upon entry of a query in a search engine. The text matching process may assign a match score or value to the reference text strings representative of their textual relevance to the partial input text. System 100 may be configured to determine suggested input strings from among the reference strings based on a combination of the frequency values and the associated with the reference strings and the match scores assigned by the text matching process. In some embodiments, system 100 may be configured to generate a combined score for use in selecting reference text strings as suggestions based on a weighted combination of the frequency values and match scores. For example, in one embodiment, the frequency values and match scores may be normalized, a first weight may be applied to the frequency values (e.g., 70 percent), a second weight may be applied to the match scores (e.g., 30 percent), combined values may be obtained for each reference string by summing the weighted values, and two or more reference strings having the highest combined values may be selected as suggested input strings. In some embodiments, system 100 may select a reference string as a suggested input string to be presented to the user even if the reference string does not include an exact match for the partial input string (e.g., if the reference string has a high frequency measure).

In some embodiments, system 100 may be configured to determine suggested input strings from among the reference strings based in part on a location in which the partial textual input is provided. For example, the partial textual input may be provided within a text entry field within a data form, and the data form may have multiple text entry field portions (e.g., multiple separate text entry input boxes, multiple lines within a text entry field, etc.). In some embodiments, in addition to or instead of identifying a frequency with which the reference text strings appear generally within reference files 130, system 100 may identify a frequency with which the reference strings appear within certain portions of reference files 130 (e.g., certain types of data fields, certain parts of the data fields, etc.). In one exemplary embodiment relating to ECG images, it may be very common for the first line of text input relating to an ECG image to be a statement describing a type of heart rhythm associated with the ECG image. In some such embodiments, system 100 may be configured to generate suggestions based on frequencies of appearance of the reference strings within the first line of input within reference files 130. Because the first line of input within reference files 130, within this exemplary embodiment, frequently is a text string relating to heart rhythms, many or all of the top suggestions provided to the user will be rhythm-related text strings. In some embodiments, rules may be applied by suggestion module 115 to suggestions provided in certain portions of the data form. For example, if it is known that all or nearly all text entries in the first line of a data form relate to a heart rhythm, suggestion module 115 may restrict the reference strings that may be selected for suggestions for partial textual input in the first line of a data form to those that relate to heart rhythms. In another example, if it is known that a certain portion of a medication reporting form always, or nearly always, includes text relating to a certain type of medication or patient characteristic, suggestion module 115 may restrict the reference strings that may be selected as suggestions for that portion of the form to phrases relating to that type of medication or patient characteristic. In some embodiments, system 100 may allow a user to enter textual input into a data form having two or more data fields (e.g., separate data entry boxes), and the suggestions provided may depend upon the data entry field into which the partial textual input was entered.

In some embodiments, system 100 may be configured to determine suggestions for completing partial text entry in one portion of a data entry field or form based on text entered into another portion of the field/form. For example, if a user (or an automated medical data analysis process) entered a first text string into a first line of a data entry field, suggestions for a partial textual input into the second line of the field may be determined based in part on the content of the first line text. Text entered in one portion of the form may increase or decrease a likelihood that particular reference strings are the text the user intends to enter in another portion of the form. In some embodiments, suggestion module 115 may be configured to determine frequency measures for reference strings with respect to other reference strings. For example, a particular reference string A may appear in only five percent of reference files generally, but may appear in 75 percent of reference files where a reference string B appears in the previous line. In another example, a reference string C may appear in 25 percent of reference files generally, but may appear in no files that include a reference string D. In some embodiments, system 100 may be configured to determine suggestions for completing the partial input based in part on the relative frequency measure of the reference strings with respect to other reference strings or a combination of the relative frequency measure and the general frequency measure.

In some embodiments, system 100 may be configured to generate suggested input strings for a user based on one or more user-specific files 135. A user may include an individual (e.g., a particular physician) and/or an institution (e.g., a business, organization, or other entity, such as a hospital, health system, or research institution). As a user utilizes system 100 to enter data relating to medical data, the data may be stored in user-specific files 135 (e.g., within database 125) for later use in generating suggestions. When a partial textual input is received from the user, system 100 may determine suggestions for completing the input based on user-specific files 135, alone or in combination with the other general reference files 130 stored in database 125. By utilizing user-specific files 135, system 100 may be able to produce suggestions that are more customized to the user and/or more likely to match the text the user intends to enter. For example, the user may regularly enter one or more text strings that are unique from text entered by other users and are not reflected in the general reference files 130, but that text may be reflected in user-specific reference files 135 and may be provided as suggestions based on those files.

Figure 4:
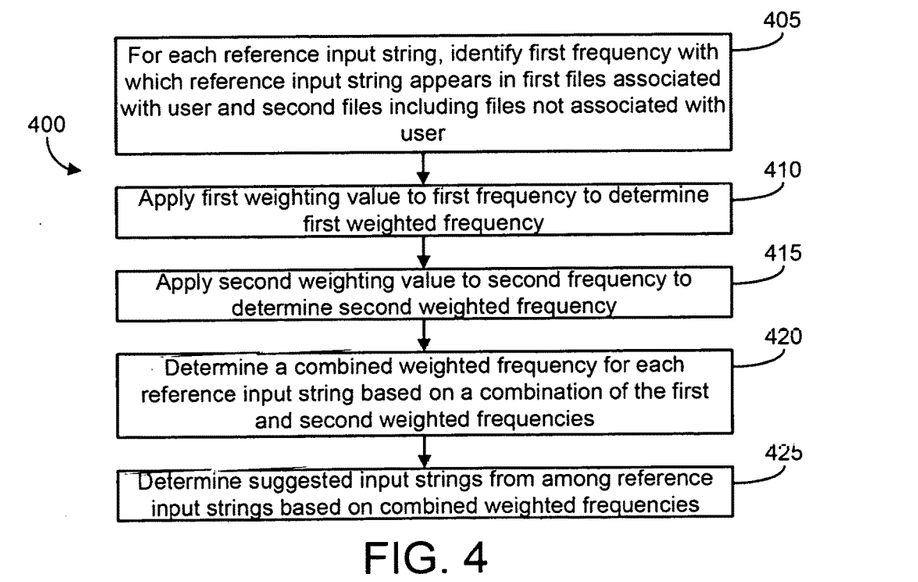
FIG. 4 is a flow diagram of a process for determining suggested input strings based on comparison of partial textual input with reference input from a first set of files associated with the user and a second set of files including files not associated with the user according to an exemplary embodiment.

In some embodiments, system 100 may be configured to determine suggestions from among the reference strings based on a weighted combination of the frequency values from user-specific files 135 and general reference files 130 (e.g., data files not associated with the user, or a combination of data files associated with the user and not associated with the user). Referring now to FIG. 4, a process 400 is shown for determining suggestions based on such a weighted combination according to an exemplary embodiment. For each reference input string, system 100 may be configured to identify a first frequency value representing a frequency with which the reference string appears in files associated with the user and a second frequency value representing a frequency with which the reference string appears in a group of files including at least some files not associated with the user (e.g., general reference files within a database) (405). System 100 may apply a first weighting value to the first frequency value to determine a first weighted value (410) and a second weighting value to the second frequency value to determine a second weighted value (415). For example, system 100 may apply a weight of 60 percent to the user-specific frequency values and a weight of 40 percent to the general frequency values. System 100 may then determine a combined weighted frequency for each reference input string based on a combination (e.g., sum) of the first and second weighted frequency values (420). System 100 may determine the suggested input strings from among the reference strings based on the combined weighted frequencies (425).

In some embodiments, system 100 may be configured to determine suggestions to provide form completing the partial text input based in part on one or more characteristics (e.g., waveform characteristics) associated with the medical data (e.g., medical image and/or underlying signals of the medical data. For example, medical data analysis module 120 may be configured to analyze a medical image and determine one or more characteristics associated with an image waveform. In some embodiments, medical data analysis module 120 may analyze a particular ECG image and determine that the waveform of the image is associated with a particular type of heart arrhythmia. In some embodiments, system 100 may be configured to determine suggested input strings to complete the partial input using only reference files for images that are associated with the same type of arrhythmia. In some embodiments, system 100 may include both general reference files and the reference files associated with the same arrhythmia type in generating suggestions, but may provide a greater weight (e.g., using weighting values) to frequency results for the reference files associated with the same arrhythmia type. In some embodiments, the determination of whether reference files are associated with a particular condition may be based on text searching of the text in the files and/or on tags or other metadata associated with the files (e.g., entered by a user or tagged based on automated analysis).

Figure 5:
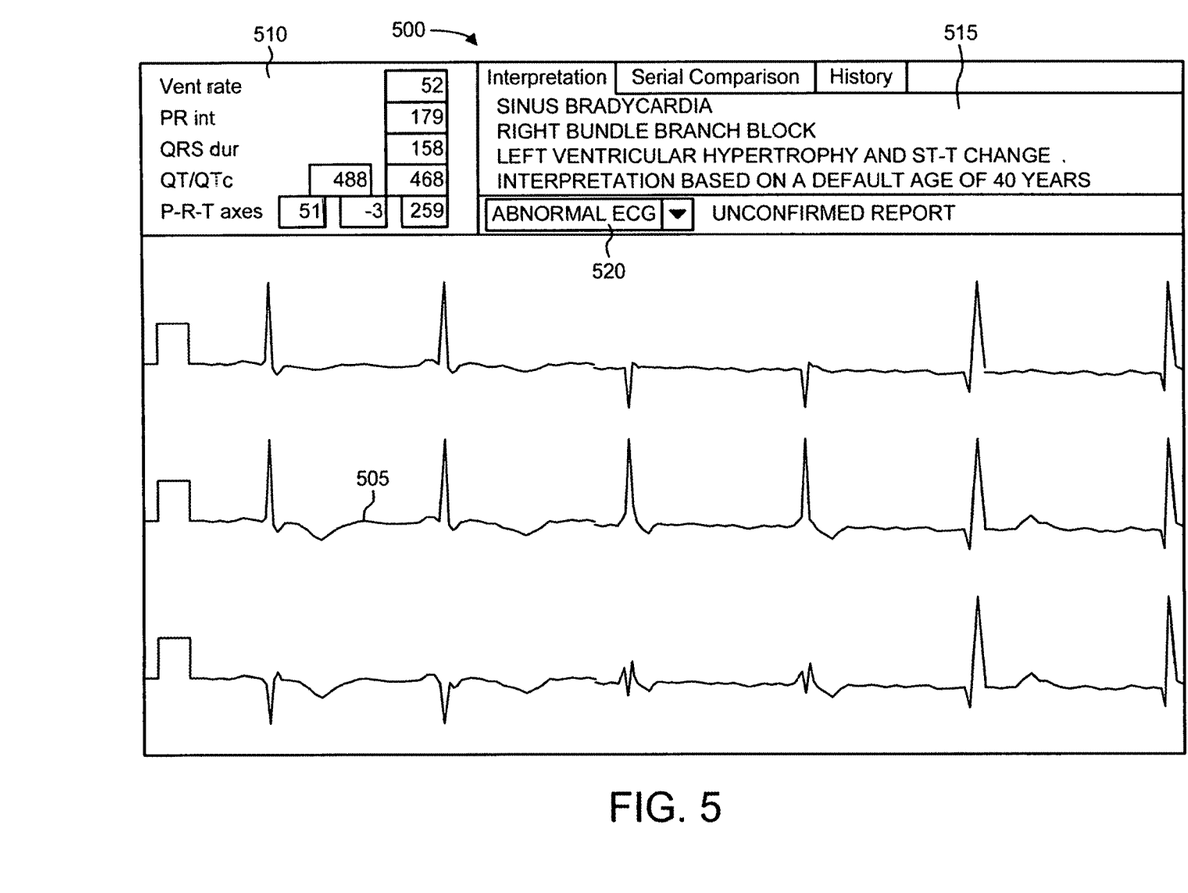
FIG. 5 is an illustration of a user interface in which textual data relating to a medical image can be entered according to an exemplary embodiment.
Figure 6:
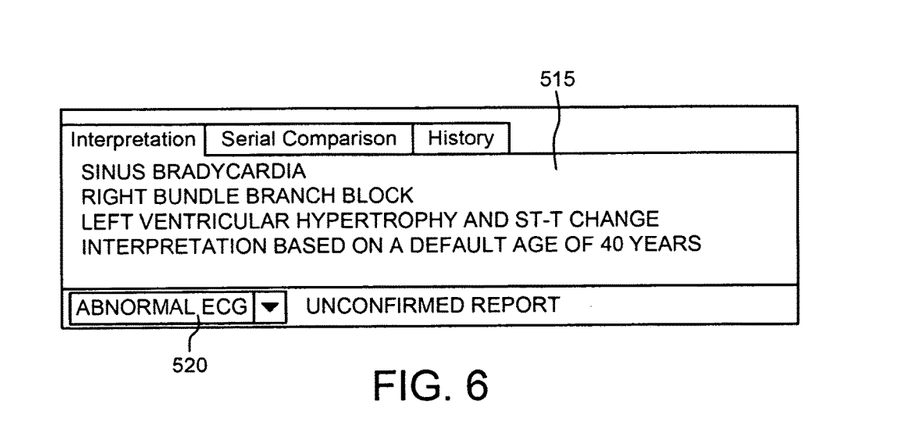
FIG. 6 is an illustration of the text entry field shown in FIG. 5 according to an exemplary embodiment.

FIGS. 5 through 10 provide example illustrations of user interfaces into which users may provide text relating to medical images according to exemplary embodiments. Referring specifically to FIG. 5, a display image 500 of a reporting system interface is shown according to an exemplary embodiment. Display image 500 includes an ECG image 505 showing a visual representation of an ECG signal and a measurement portion 510 providing various measurements relating to ECG image 505. Display image 500 also includes a text input interface 515 into which text relating to ECG image 505 can be entered. In the illustrated exemplary embodiment, text input interface 515 has been pre-populated based upon an automated analysis of ECG image 505. In some embodiments, display image 500 may include a menu 520 providing a user with a pre-populated list of one or more descriptive tags or textual entries that may be added within interface 515. FIG. 6 illustrates an enlarged view of text input interface 515.

Figure 7:
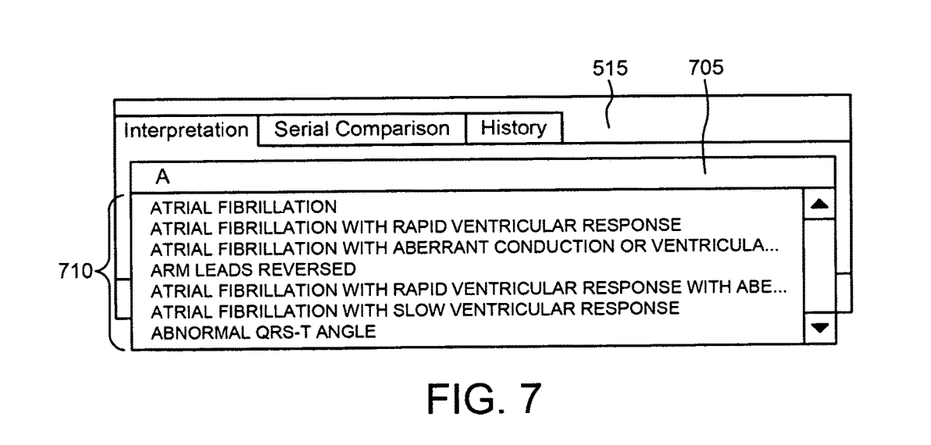
FIG. 7 is an illustration of the text entry field shown in FIG. 5 in which a first partial textual input has been entered according to an exemplary embodiment.
Figure 8:
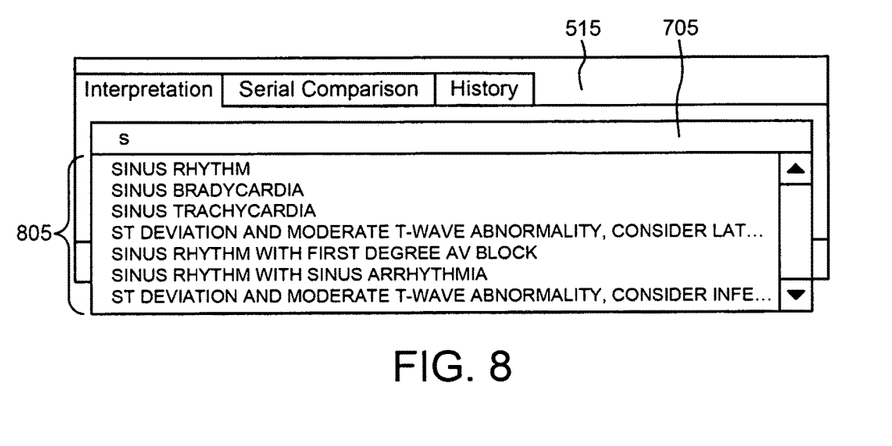
FIG. 8 is an illustration of the text entry field shown in FIG. 5 in which a second partial textual input has been entered according to an exemplary embodiment.
Figure 9:
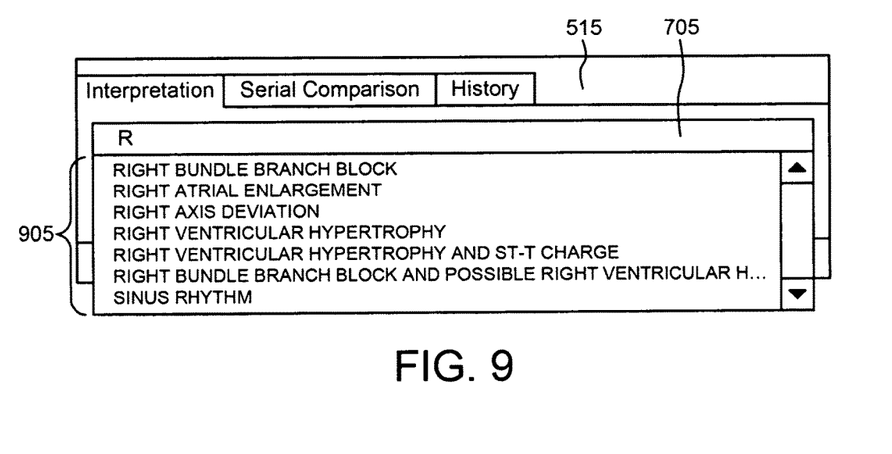
FIG. 9 is an illustration of the text entry field shown in FIG. 5 in which a third partial textual input has been entered according to an exemplary embodiment.

FIG. 7 illustrates a first example of suggestions 710 that may be presented to a user upon entry of the partial textual input "A" within a text input field 705 of interface 515. Five of the top seven suggestions provided to the user include the terms "atrial fibrillation," indicating that reference strings including the terms "atrial fibrillation" appear commonly in the database used in generating the suggestions. In some embodiments, the scrollbar on the right side of the suggestion box may be used to scroll down and view additional suggestions. FIG. 8 illustrates a second example of suggestions 805 associated with the partial textual input "S," and FIG. 9 illustrates a third example of suggestions 905 associated with a partial textual input "R." FIG. 9 illustrates an example in which not all suggestions begin with the partial textual input; "sinus rhythm" is one of the suggestions for completing the partial textual input "R."

Figure 10:
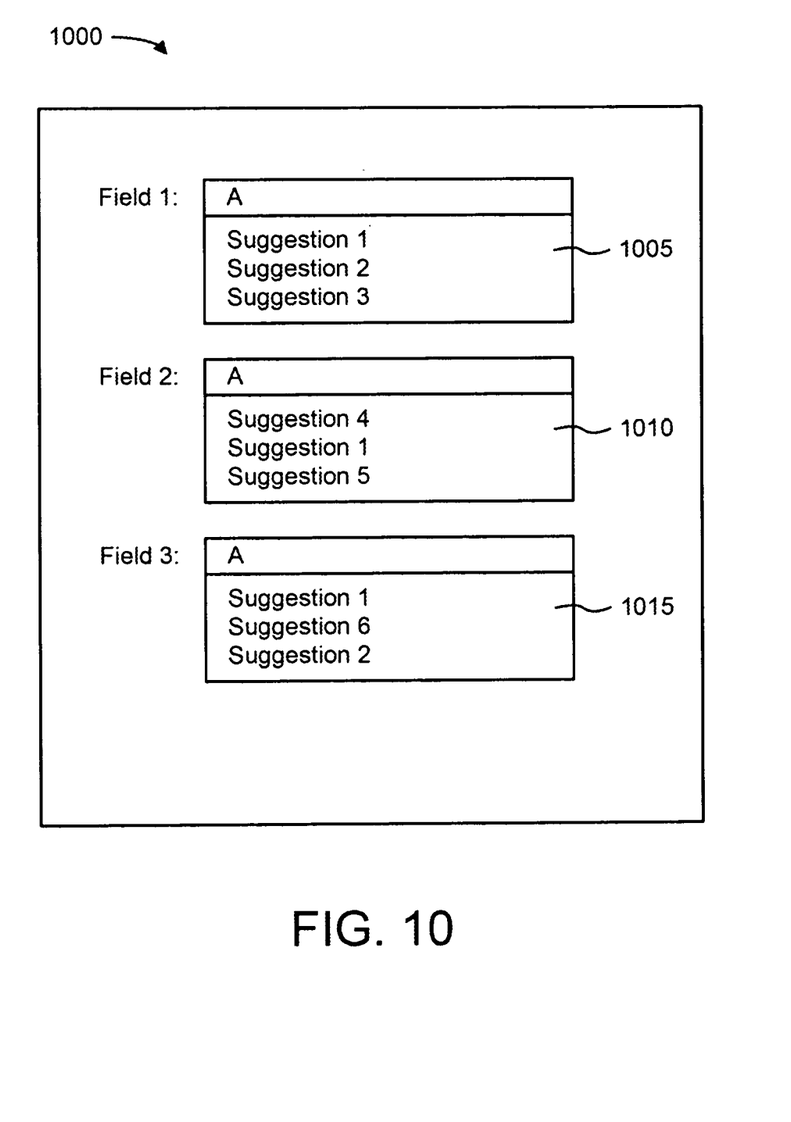
FIG. 10 is an illustration of a medical image data entry form including several text input fields according to an exemplary embodiment.

FIG. 10 illustrates an example data entry form 1000 including several fields 1005, 1010, and 1015 into which text relating to a medical image can be input according to an exemplary embodiment. As illustrated in FIG. 10, in some embodiments, the same partial textual input provided in different fields may result in different suggestions based on the field. For example, the partial textual input "A" results in suggestions 1, 2, and 3 in field 1005, suggestions 4, 1, and 4 in field 1010, and suggestions 1, 6, and 2 in field 1015. The different suggestions may result from different frequencies of appearance of different reference strings in the different input fields within reference files in a database used to generate the suggestions. In some embodiments, suggestions provided in one field (e.g., field 1015) may be determined based in part on text input in one or more other fields (e.g., fields 1005 and/or 1010).

While the discussion above has focused primarily on exemplary embodiments relating to medical images, the systems and methods described herein may be applied equally to other types of medical data. For example, in some embodiments, an exemplary system may be configured to assist with textual entry relating to patient medications. In one such example, a patient may enter a partial textual input "Le," and the system may provide a list of suggestions having "Levatol" (a beta blocker commonly prescribed for hypertension, which is a common disease state) at the top of the list based on analysis of example medication-related data in a database in which "Levatol" appears with a high frequency. In another example, in response to the partial input "E," the system may provide a list that includes "Erythromycin," a common antibiotic, at a higher position than "Eczemol," a drug used to treat eczema, based on "Erythromycin" appearing with higher frequency than "Eczemol" in a reference database. In some embodiments, the system may be configured to assist with textual entry for patient history and physical charting. In one such example, in response to the partial input "H," the system may suggest "Hypertension" high on a list of suggestions, as hypertension is a common disease state. The systems and methods described herein may be applied to various other types of medical data reporting and analysis applications in various other embodiments, and all such applications are contemplated within the scope of the present disclosure.

The disclosure is described above with reference to drawings. These drawings illustrate certain details of specific embodiments that implement the systems and methods and programs of the present disclosure. However, describing the disclosure with drawings should not be construed as imposing on the disclosure any limitations that may be present in the drawings. The present disclosure contemplates methods, systems, and program products on any machine-readable media for accomplishing its operations. The embodiments of the present disclosure may be implemented using an existing computer processor, or by a special purpose computer processor incorporated for this or another purpose or by a hardwired system. No claim element herein is to be construed under the provisions of 35 U.S.C. § 112, sixth paragraph, unless the element is expressly recited using the phrase "means for." Furthermore, no element, component or method step in the present disclosure is intended to be dedicated to the public, regardless of whether the element, component or method step is explicitly recited in the claims.

As noted above, embodiments within the scope of the present disclosure include program products comprising machine-readable storage media for carrying or having machine-executable instructions or data structures stored thereon. Such machine-readable storage media can be any available media that can be accessed by a general purpose or special purpose computer or other machine with a processor. By way of example, such machine-readable storage media can include RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable storage media. Machine-executable instructions include, for example, instructions and data which cause a general purpose computer, special purpose computer, or special purpose processing machine to perform a certain function or group of functions. Machine or computer-readable storage media, as referenced herein, do not include transitory media (i.e., signals in space).

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM) or other non-transitory storage medium. The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing description of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

What is claimed is:

1. A method comprising:
  receiving, at a computing device and from a user, a partial textual input relating to medical data comprising a medical image, the medical image comprising a waveform, the partial textual input comprising a string of one or more characters;
  determining, using the computing device, one or more most clinically common input strings associated with the partial textual input, wherein determining the one or more most clinically common input strings comprises:

analyzing the waveform of the medical image to determine a type of arrhythmia for the medical image;

identifying, within a database, a plurality of reference files matching the determined type of arrhythmia for the medical image, wherein the plurality of reference files comprise different textual data relating to the determined type of arrhythmia in reference medical images;

for each reference input string of a plurality of reference input strings contained within one or more of the plurality of reference files, identifying a frequency with which the reference input string appears in the identified plurality of reference files; and determining the one or more most clinically common input strings from among the plurality of reference input strings based on the frequencies with which the reference input strings appear in the identified plurality of reference files, such that the one or more most clinically common input strings are determined from reference files matching the type of arrhythmia for the medical image to which the partial textual input relates; and providing the one or more most clinically common input strings to the user as suggestions for completing the partial textual input.

2. The method of claim 1, further comprising providing the user with one or more suggested textual strings based on automated analysis of the medical data, wherein receiving the partial textual input comprises receiving a modification from the user to at least one of the one or more suggested textual strings to produce at least one modified suggested textual string, and wherein determining the one or more most clinically common input strings associated with the partial textual input comprises determining the one or more most clinically common input strings associated with the at least one modified suggested textual string.

3. The method of claim 1, wherein the partial textual input is received within a data form, and wherein determining the one or more most clinically common input strings associated with the partial textual input comprises determining the one or more most clinically common input strings based in part on a portion of the data form within which the user provided the partial textual input.

4. The method of claim 3, wherein the partial textual input is received within one of a plurality of portions of the data form, and wherein determining the one or more most clinically common input strings associated with the partial textual input comprises determining the one or more most clinically common input strings based in part on textual input received within another of the plurality of portions of the data form.

5. The method of claim 1, wherein determining the one or more most clinically common input strings associated with the partial textual input comprises determining the one or more most clinically common input strings based in part on the user.

6. The method of claim 5, wherein the user comprises at least one of an individual or an institution.

7. The method of claim 5, wherein at least a portion of the plurality of reference files are files associated with the user.

8. The method of claim 7, wherein the plurality of reference files comprises a first plurality of reference files associated with the user and a second plurality of reference files comprising files not associated with the user, and wherein determining the one or more most clinically common input strings comprises:

for each of the plurality of reference input strings:
identifying a first frequency with which the reference input string appears in the first plurality of reference files and a second frequency with which the reference input string appears in the second plurality of reference files;

applying a first weighting value to the first frequency to determine a first weighted frequency;

applying a second weighting value to the second frequency to determine a second weighted frequency; and determining a combined weighted frequency for the reference input string based on a combination of the first weighted frequency and the second weighted frequency; and determining the one or more most clinically common input strings from among the plurality of reference input strings based on the combined weighted frequencies.

9. The method of claim 1, wherein the medical data to which the partial textual input relates comprises an electrocardiogram (ECG) image.

10. A system comprising:
an electronic processor operably coupled to at least one memory and configured to:
receive, from a user, a partial textual input relating to medical data comprising a medical image, the medical image comprising a waveform, the partial textual input comprising a string of one or more characters;

determine one or more suggested input strings associated with the partial textual input by:
analyzing the waveform of the medical image to determine a type of arrhythmia for the medical image;

identifying, within a database, a plurality of reference files matching the determined type of arrhythmia for the medical image, the plurality of reference files comprising a plurality of reference input strings, wherein the plurality of reference files comprise different textual data relating to the determined type of arrhythmia in reference medical images;

for each reference input string, identifying a frequency with which the reference input string appears in the plurality of reference files; and determining the one or more suggested input strings from among the plurality of reference input strings based on the frequencies with which the reference input strings appear in the plurality of reference files; and provide the one or more suggested input strings to the user as suggestions for completing the partial textual input.

11. The system of claim 10, wherein the electronic processor is configured to provide the user with one or more initial textual strings based on automated analysis of the medical data, wherein the electronic processor is configured to receive the partial textual input by receiving a modification from the user to at least one of the one or more initial textual strings to produce at least one modified textual string, and wherein the electronic processor is configured to determine the one or more suggested input strings associated with the partial textual input by determining the one or more suggested input strings associated with the at least one modified textual string.

12. The system of claim 10, wherein the electronic processor is configured to determine the one or more suggested input strings based in part on the user, wherein the user comprises at least one of an individual and an institution, and wherein at least a portion of the plurality of reference files are files associated with the user.

13. The system of claim 10, wherein the partial textual input is received within a data form, and wherein the electronic processor is configured to determine the one or more suggested input strings based in part on a portion of the data form within which the user provided the partial textual input.

14. The system of claim 13, wherein the data form comprises a plurality of input fields, wherein the partial textual input is received within a first input field of the plurality of input fields, wherein two or more of the plurality of reference files comprise a data field corresponding to the first input field of the data form, and wherein the electronic processor is configured to determine the one or more suggested input strings associated with the partial textual input by:
- for each of the plurality of reference input strings, identifying a frequency with which the reference input string appears in the data field corresponding to the first input field in the plurality of reference files; and
- determining the one or more suggested input strings from among the plurality of reference input strings based on the frequencies with which the reference input strings appear in the data field corresponding to the first input field within the plurality of reference files.

15. The system of claim 10, wherein the medical data to which the partial textual input relates comprises an electrocardiogram (ECG) image.

16. One or more computer-readable storage media having instructions stored thereon, the instructions being executable by one or more processors to:
- receive, from a user comprising at least one of an individual or an institution, a partial textual input relating to a medical image, the medical image comprising a waveform, the partial textual input comprising a string of one or more characters;
- determine one or more suggested input strings associated with the partial textual input by:
  - analyzing the waveform of the medical image to determine a type of arrhythmia for the medical image;
  - identifying, within a database, a plurality of reference files matching the determined type of arrhythmia for the medical image, the plurality of reference files comprising a plurality of reference input strings, wherein the plurality of reference files comprise different textual data relating to the determined type of arrhythmia in reference medical images;
  - for each reference input string of a plurality of reference input strings contained within one or more of a plurality of reference files within a database, identifying a frequency with which the reference input string appears in the plurality of reference files, wherein the plurality of reference files comprise different textual data relating to the determined type of arrhythmia in reference medical images; and
  - determining the one or more suggested input strings from among the plurality of reference input strings based on the frequencies with which the reference input strings appear in the plurality of reference files, such that the one or more suggested input strings are determined from reference files matching the type of arrhythmia for the medical image to which the partial textual input relates; and
- provide the one or more suggested input strings to the user as suggestions for completing the partial textual input.

17. The one or more computer-readable storage media of claim 16, wherein the instructions are configured to cause the one or more processors to provide the user with one or more initial textual strings based on automated analysis of the medical image, wherein the instructions are configured to cause the one or more processors to receive the partial textual input by receiving a modification from the user to at least one of the one or more initial textual strings to produce at least one modified textual string, and wherein the instructions are configured to cause the one or more processors to determine the one or more suggested input strings associated with the partial textual input by determining the one or more suggested input strings associated with the at least one modified textual string.

18. The one or more computer-readable storage media of claim 16, wherein the partial textual input is received within a data form, and wherein the instructions are configured to cause the one or more processors to determine the one or more suggested input strings based in part on a portion of the data form within which the user provided the partial textual input.

19. The one or more computer-readable storage media of claim 16, wherein the medical data to which the partial textual input relates comprises an electrocardiogram (ECG) image.

20. The one or more computer-readable storage media of claim 16, wherein the instructions are configured to cause the one or more processors to determine the one or more suggested input strings based in part on the user, wherein the user comprises at least one of an individual and an institution, and wherein at least a portion of the plurality of reference files are files associated with the user.

* * * * *